United States Patent [19]

Tsukamoto et al.

[11] Patent Number: 4,799,790
[45] Date of Patent: Jan. 24, 1989

[54] CHROMATIC DISPERSION MEASURING SYSTEM FOR OPTICAL FIBERS

[75] Inventors: Takeshi Tsukamoto, Hadano; Takao Tanimoto, Sagamihara, both of Japan

[73] Assignee: Anritsu Corporation, Tokyo, Japan

[21] Appl. No.: 159,838

[22] Filed: Feb. 24, 1988

[30] Foreign Application Priority Data

Feb. 27, 1987 [JP] Japan .................................. 62-44569

[51] Int. Cl.[4] ........................................... G01N 21/84
[52] U.S. Cl. .................................................. 356/73.1
[58] Field of Search ....................................... 356/73.1

[56] References Cited

U.S. PATENT DOCUMENTS 4,551,019 11/1985 Vella et al. ........................... 356/73.1

OTHER PUBLICATIONS

The Paper 2188 of 1984 All National Meeting of Electronics and Communications Engineers of Japan, entitled "Chromatic Dispersion Measurement for Singlemode Fiber", Tanaka & Kitayama.

Primary Examiner—Vincent P. McGraw
Attorney, Agent, or Firm—Frishauf, Holtz, Goodman & Woodward

[57] ABSTRACT

A system for measuring a chromatic dispersion of an optical fiber has a light signal transmitter and a light signal receiver. The transmitter has a modulation signal generating circuit for generating at least one modulation signal having a predetermined frequency, and synchronizing signal generating circuit for generating a synchronizing signal having a predetermined frequency. First adding circuit is provided for adding the synchronizing signal generated by the synchronizing signal generating circuit to the modulation signal generated by the modulation signal generatig circuit. The light signal receiver has first photoelectric converter for converting the reference optical signal into a reference electrical signal added with the synchronizing signal and second photoelectric converter for converting the measurement optical signal into a measurement electrical signal added with the synchronizing signal. The receiver also has a synchronizing signal regenerating circuit for generating a regenerated synchronizing signal at a predetermined timing, and local signal generating circuit for generating at least one local signal having a predetermined frequency. Second adding circuit is provided for adding the regenerated synchronizing signal to the local signal from the local signal generating circuit. Further, a timing signal obtaining circuit is provided for separating the synchronizing signal from the reference electrical signal added with the synchronizing signal from the first photoelectric converter to obtain a timing signal serving as the synchronizing signal, in order to provide the predetermined timing to the synchronizing signal regenerating means.

19 Claims, 7 Drawing Sheets

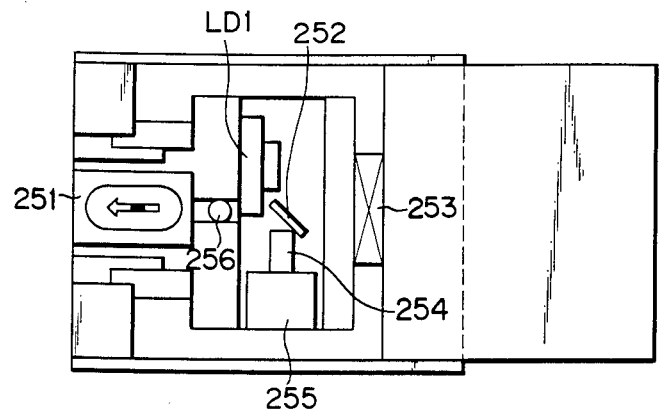
F I G. 4A
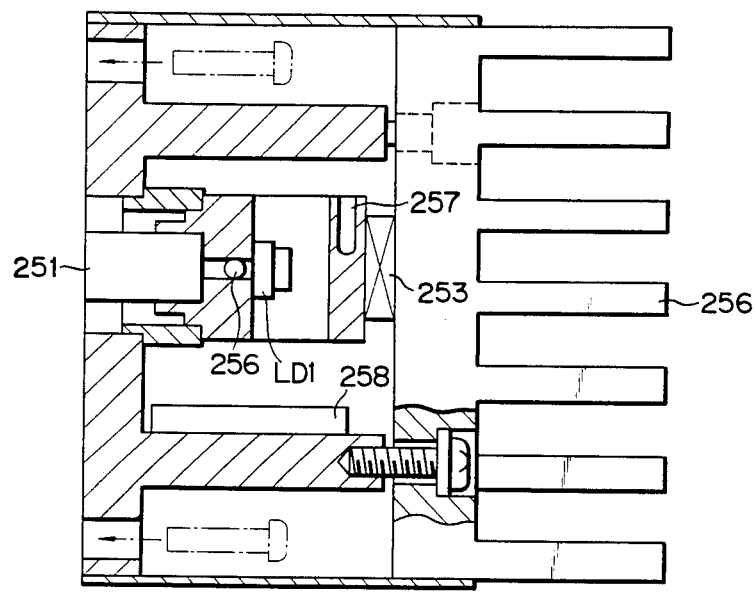
F I G. 4B

CHROMATIC DISPERSION MEASURING SYSTEM FOR OPTICAL FIBERS

BACKGROUND OF THE INVENTION

1. Field of the Invention

The present invention relates to a system for measuring chromatic dispersion of an optical fiber and, more particularly, to a system for measuring a chromatic dispersion of an optical fiber based on a baseband phase comparison method.

2. Description of the Related Art

The chromatic dispersion characteristics of optical fibers are important for determining an information transmission speed of an optical fiber communication path. The following are the main methods used at present for measuring chromatic dispersion in single-mode optical fibers:

(1) A pulse delay time difference measurement method using a fiber Raman laser/spectroscope combination;

(2) A baseband phase comparison method using an LED (light-emitting diode)/spectroscope combination;

(3) A baseband phase comparison method using multiple LDs (laser diodes) of different wavelengths; and (4) An interference method using the interference characteristics of light.

Of these methods, the baseband phase comparison method (3) will be described below. In general, optical signals having different wavelengths differ in group velocity due to material dispersion and waveguide dispersion, resulting in phase differences of the optical signals after their propagation through an optical fiber. The baseband phase comparison method utilizes this fact. Optical signal generators, e.g., LDs having different wavelengths are arranged in an optical signal transmitter, and two types of optical signals, i.e., a reference optical signal and a measurement optical signal, which are intensity-modulated by a sine wave modulation signal, are generated. The two types of optical signals are incident on a reference optical fiber and a measurement optical fiber, respectively. In an optical signal receiver, a group delay time difference is calculated from a phase difference between the wavelengths after propagation through the measurement optical fiber. The measurement result is approximated by appropriate function $\tau(\lambda)$, and the function is analytically differentiated to obtain a target chromatic dispersion characteristics $D(\lambda) = d\tau(\lambda)/d\lambda$. The graph in FIG. 2 represents the relationship between the group delay time difference and the wavelengths.

In the baseband phase comparison method, when measurement is done for an installed optical fiber by the far-end method, it is required to conduct synchronization between the transmitter and the receiver. When the transmitter and the receiver are to be synchronized, a cable or radio communication means is provided between the transmitter and the receiver to allow communication therebetween. Thus, setting of the modulation signal and wavelengths, and setting of the local signal at the receiver are manually performed. However, if the numbers of frequencies and wavelengths of the modulation signal subjected to measurement are increased, the measurement operation is much complicated. Thus, measurement of the chromatic dispersion requires much time. Furthermore, since the parameters are manually set, they may be erroneously set. In addition, since such erroneous setting cannot be checked, the reliability of the measurement result cannot be determined.

SUMMARY OF THE INVENTION

It is therefore an object of the present invention to provide an automatic chromatic dispersion measuring system in which erroneous setting by manual operation can be avoided.

It is another object of the present invention to provide a chromatic dispersion measuring system requiring less time in measuring.

In accordance with the present invention, a system for measuring a chromatic dispersion of an optical fiber based on a baseband phase comparison method comprises a light signal transmitter, a light signal receiver, a reference fiber, and a measurement fiber.

The transmitter comprises light source means for selectively generating one of measurement optical signals having wavelengths corresponding to n wavelength points to be measured and a reference optical signal in a predetermined combination, modulation signal generating means for generating at least one modulation signal having a predetermined frequency, synchronizing signal generating means for generating a synchronizing signal having a predetermined frequency, first adding means, connected to said modulation signal generating means and said synchronizing signal generating means, for adding the synchronizing signal generated by said synchronizing signal generating means to the modulation signal generated by said modulation signal generating means, first control signal generating means for designating the predetermined combination of one of the measurement optical signals and the reference optical signal, light source switching means, which is coupled between said light source means, said adding means, and first control signal generating means, for selectively supplying the modulation signal added with the synchronizing signal to the light source means corresponding to the combination of one of the measurement optical signals and the reference optical signal designated in accordance with the first control signal, second control signal generating means for generating a second control signal having a predetermined synchronous relation with the first control signal, and optical switch means, which has reference optical signal input and measurement optical signal inputs which are arranged in correspondence with said light source means, a measurement optical signal output, and a reference optical signal output, for, in response to the second control signal from said second control signal generating means, commonly outputting, to the measurement optical signal output, the measurement optical signal which is output from the designated one of said light source means and is selectively input to the measurement optical signal input, and outputting the reference optical signal from the reference optical signal input to the reference optical signal output. The reference optical fiber has one end and the other end, the other end of said reference optical fiber being connected to said reference optical signal output of said optical switch means so as to input the reference optical signal to the one end of said reference optical fiber. The measurement optical fiber has one end and the other end, the other end of said measurement optical fiber being connected to the measurement optical signal output of said optical switch means so as to input the measurement optical signal to the one end of said measurement optical fiber. The light signal receiver comprises first photoelectric conversion means for receiving a reference optical signal which is modulated by a modulation signal added with a synchronizing signal and converting the reference optical signal into a reference electrical signal added with the synchronizing signal, second photoelectric conversion means for receiving a measurement optical signal which is modulated by a modulation signal added with a synchronizing signal and converting the measurement optical signal into a measurement electrical signal added with the synchronizing signal, synchronizing signal regenerating means for generating a regenerated synchronizing signal at a predetermined timing, local signal generating means for generating at least one local signal having a predetermined frequency, second adding means, coupled to said local signal generating means and said synchronizing signal regenerating means, for adding the regenerated synchronizing signal to the local signal from said local signal generating means, first demodulating means, coupled to said first photoelectric conversion means and said second adding means, for receiving the local added with the regenerated synchronizing signal and receiving the reference electrical signal added with the synchronizing signal from said first photoelectric conversion means so as to perform demodulation of the reference electrical signal added with the synchronizing signal, second demodulating means, coupled to said second photoelectric conversion means and said second adding means, for receiving the local signal added with the regenerated synchronizing signal and receiving the measurement electrical signal added with the synchronizing signal from said second photoelectric conversion means so as to perform demodulation of the measurement electrical signal added with the synchronizing signal, and timing signal obtaining means, connected to said second demodulating means and said synchronizing signal regenerating means, for separating the synchronizing signal from the reference electrical signal added with the synchronizing signal from said first photoelectric conversion means to obtain a timing signal serving as the synchronizing signal, in order to provide the predetermined timing to said synchronizing signal regenerating means.

BRIEF DESCRIPTION OF THE DRAWINGS

Various advantages of the present invention will become apparent to one skilled in the art upon reading the following specification and by reference to the following drawings in which:

FIGS. 4A and 4B are views showing an arrangement of a light source used in the chromatic dispersion measuring system of the present invention;

DETAILED DESCRIPTION OF THE PREFERRED EMBODIMENTS

Figure 1:
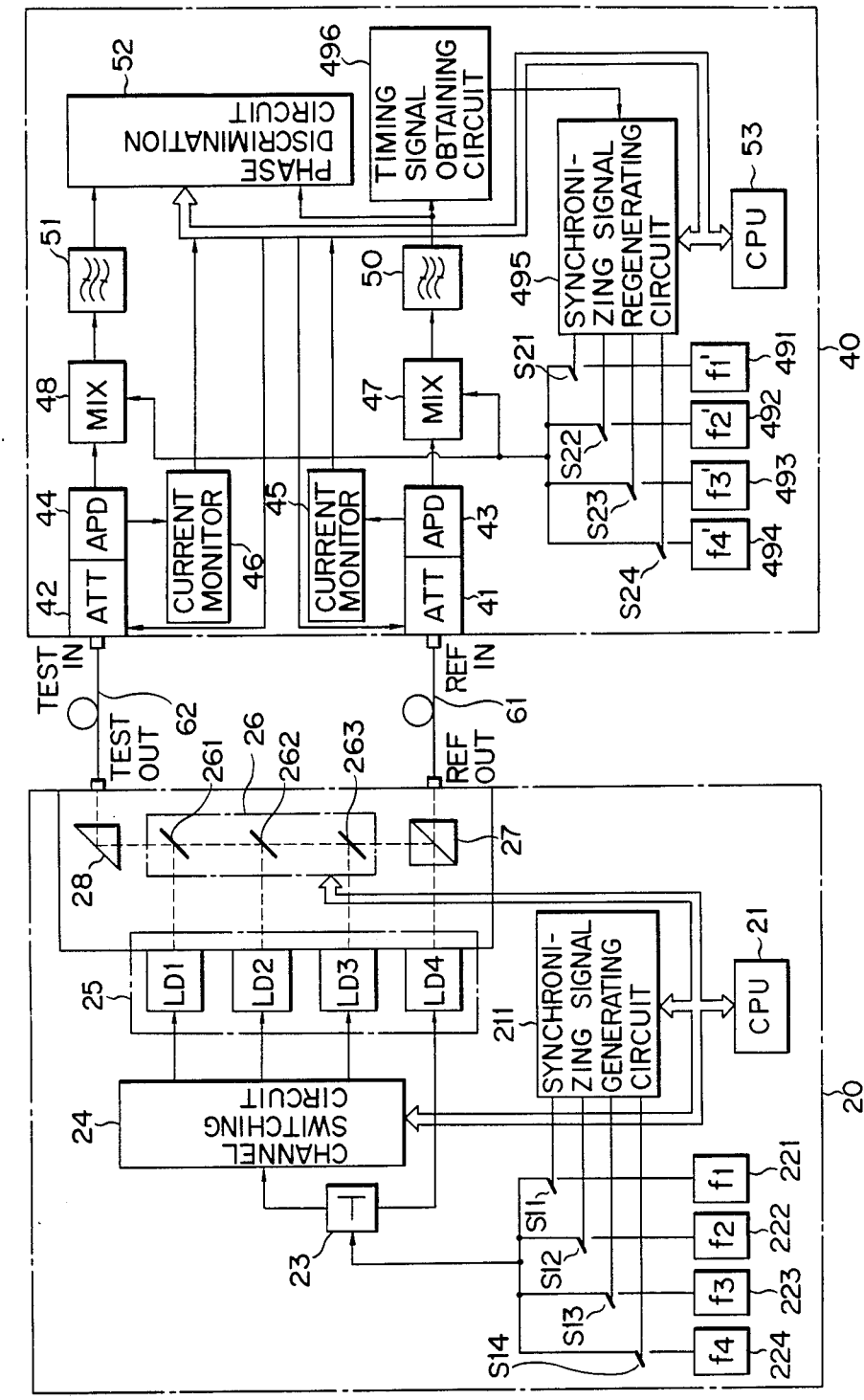
FIG. 1 is a block diagram showing a chromatic dispersion measuring system according to an embodiment of the present invention.

Referring to FIG. 1, one end of reference optical fiber 61 is connected to reference optical signal output terminal REF OUT of optical signal transmitter 20 of a chromatic dispersion measuring system of the present invention. One end of measurement optical fiber 62 is connected to measurement optical signal output terminal TEST OUT of transmitter 20. The other end of reference fiber 61 is connected to reference optical signal input terminal REF IN of optical signal receiver 40 of the system of the present invention, and the other end of measurement fiber 62 is connected to measurement optical signal input terminal TEST IN of receiver 40.

Transmission section 20 of the chromatic dispersion measuring system of the present invention will be described. Modulation signal generating circuits 221 to 224 are constituted by four quartz oscillators having four different oscillation frequencies f1 to f4. These quartz oscillators 221 to 224 are connected to 2-branching circuit 23 comprising a resistor through switches S11 to S14. One output terminal of circuit 23 is connected to channel switching circuit 24 with three outputs comprising a high-frequency relay matrix, and the other output terminal thereof is connected to laser diode LD4 of light source group 25 consisting of four laser diodes LD1 to LD4. Synchronizing signal generating circuit 211 for receiving a signal selection instruction from CPU 21 is connected to switches S11 to S14. A switching operation by channel switching circuit 4 is controlled by a switching instruction from CPU 21. In this system, 5, 50, 200, and 800 MHz are used as four frequencies f1 to f4. However, the present invention is not limited to these frequencies, and other frequencies may be employed.

As described above, 2-branching circuit 23 comprises the resistor, and channel switching circuit 24 comprises the high-frequency relay matrix. However, these circuits may comprise other proper elements. Laser diodes LD1 to LD3 of light source group 25 are arranged at the output side of channel switching circuit 24. Optical switch group 26, i.e., 261 to 263 are arranged to face the output terminals of laser diodes LD1 to LD3, respectively. Half mirror 27 is arranged at the output side of laser diode LD4 in association with optical switches 261 to 263. Furthermore, prism 28 is arranged in association with optical switches 261 to 263. Light source group 25 comprises laser diodes LD1 to LD4 but may comprise other proper light sources.

The number of laser diodes used in the chromatic dispersion measuring system of the present invention is not limited to four. The wavelengths of laser diodes LD1 to LD4 are respectively 1.26, 1.30, 1.34, and 1.53 $\mu$m in a 1.3-$\mu$m band zero dispersion wavelength optical fiber, and are respectively 1.50, 1.53, 1.56, and 1.59 $\mu$m in a 1.55-$\mu$m band zero dispersion wavelength optical fiber. However, other proper wavelengths may be employed.

FIGS. 4A and 4B show a detailed arrangement of light source group 25, each of light source group 25 includes optical isolator 251 for removing noise generated by the influence of light reflected by a corresponding one of laser diodes LD1 to LD4, spherical lens 256, mirror 252, Peltier element 253, light receiving element 255, SELFOC lens 254, thermistor 257, heat dissipating fin 256, and modulation circuit 258, in addition to laser diode, e.g., LD1.

Figure 5:
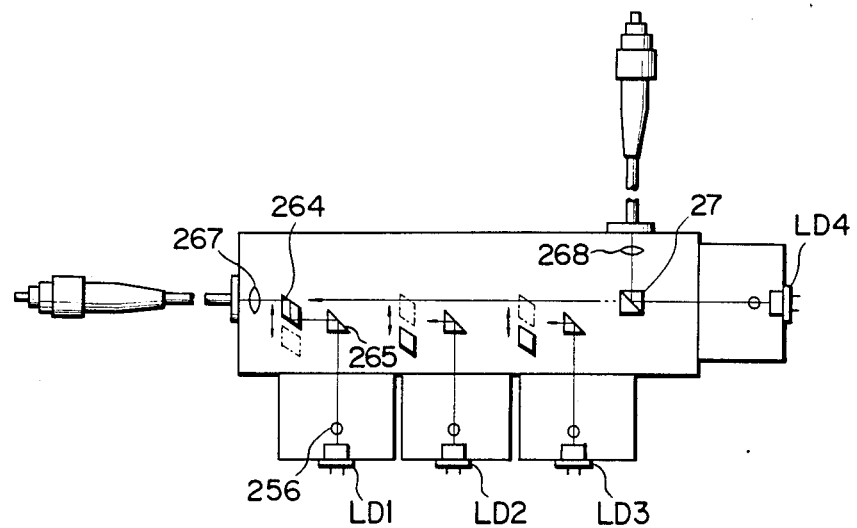
FIG. 5 is a view showing an arrangement of an optical switch used in the chromatic dispersion measuring system of the present invention.

As shown in FIG. 5, each of optical switches 261 to 263 comprises parallelogram prism, e.g., 264 arranged to shield an optical path between half mirror 27 and measurement fiber, and triangular prism, e.g., 265 arranged to be slightly shifted from parallelogram prism 64. These two prisms are arranged at positions such that light emitted from laser diodes LD1 to LD3 becomes incident on one end of measurement fiber through triangular prism 265 and parallelogram prism 264. When the light emitted from laser diode LD4 is reflected by half mirror 27 and is directed toward measurement fiber, parallelogram prism 264 is slid and shifted to release the optical path which has been shielded. Thus, the light can propagate straight from half mirror 27 to measurement fiber. Reference numeral 256 in FIG. 5 denotes a spherical lens. Reference numerals 267 and 68 denote a condensing lens.

Figure 3:
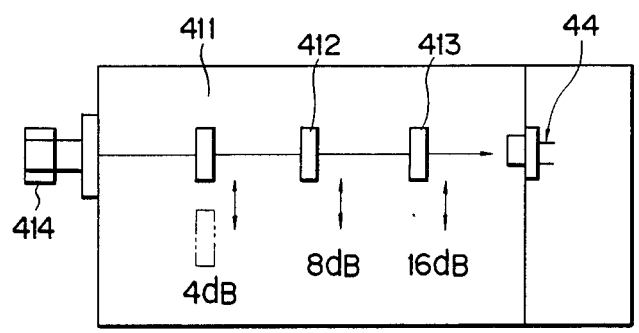
FIG. 3 is a view showing an arrangement of an attenuator according to the present invention.

In optical signal receiver 40 shown in FIG. 1, programmable optical ATTs (programmable optical attenuators) 41 and 42, at reference signal input terminal REF IN and measurement signal input terminal TEST IN of fibers 61 and 62, respectively. FIG. 3 shows more detailed attenuators 41 and 42. In each of programmable optical attenuator 41 and 42, three optical attenuation elements 411, 412, and 413 are serially arranged and are integrally coupled to, e.g., APD 44. Reference numeral 414 in FIG. 3 denotes a photoreceptacle. The diameter of each of optical attenuation elements 411, 412, and 413 is 8 mm, and attenuation values of these elements are respectively 4 dB, 8 dB, and 16 dB. However, the diameter and the attenuation values may be appropriately determined. These attenuation elements 411, 412, and 413 are programmably turned on/off, so that 8 different attenuation values can be set.

In FIG. 1, APDs 43 and 44 have a function of converting optical signals output from programmable optical attenuators 41 and 42 into electrical signals. Current monitors 45 and 46 are connected to APDs 43 and 44, respectively. Current monitors 45 and 46 detect output currents from APDs 43 and 44 to detect their signal levels, and control attenuation values of attenuators 41 and 42 in accordance with the detected levels, so that optical signals of a predetermined level can be input to APDs 43 and 44. Demodulation signals from APDs 43 and 44 are input to mixers 47 and 48, respectively. Local signal generating circuits 491 to 494 are constituted by four quartz oscillators having four different oscillation frequencies f1' to f4'. These four quartz oscillators are connected to mixers 47 and 48 respectively through switches S21 to S24. Synchronizing signal regenerating circuit 495 for receiving a control signal from CPU 55 is connected to switches S21 to S24. Mixers 47 and 48 are connected to filters 50 and 51, which are connected to phase discrimination circuit 52. Filter 50 is also connected to timing signal obtaining circuit 496. Timing signal obtaining circuit 496 is connected to synchronizing signal regenerating circuit 495. In the system of the present invention, timing signal obtaining circuit 496 comprises a PLL but may comprise another element. For the sake of best understanding of the operation of the chromatic dispersion measuring system of the present invention, the overall operation procedures will be described with reference to FIG. 1. CPU 21 supplies a signal selection instruction to synchronizing signal generating circuit 211 at a predetermined timing. Circuit 211 outputs a switch-ON control signal for a predetermined period of time to turn on a selected one of the switches, e.g., switch S11. On the switch-ON action, quartz oscillator f1 connected to switch S11 generates a f1 = 5-MHz modulation signal. Also, a 270-Hz rectangular wave signal as a synchronizing signal (FIG. 7B) is output from circuit 211 to switch S11, say, for one second after generation of the 5-MHz modulation signal. As a result, modulation signal f1 generated by modulation signal generating circuit 221 becomes an modulation signal f1 added with the synchronizing signal when it reaches 2-branching circuit 23. Modulation signal f1 is branched into two by 2-branching circuit 23, and one output from circuit 23 is supplied to relay matrix circuit 24. Relay matrix circuit 24 performs the switching operation to select one of the outputs of channel switching circuit 24 in response to a switching instruction from CPU 21. Upon receiving the selected output, one of laser diodes LD1 to LD3 corresponding to the selected output, e.g., laser diode LD1 is driven. Thus, laser diode LD1 generates an optical signal which is intensity-modulated by modulation frequency f1. The optical signal is received by optical switch 261 corresponding to laser diode LD1. As described above, optical switch 261 is selected in response to the switching instruction from the CPU21. Thereafter, the optical signal is reflected by prism 28, and is incident on one end of measurement fiber 62 through measurement optical signal output terminal TEST OUT of optical signal transmitter 20, as a measurement optical signal. On the other hand, the other output of 2-branching circuit 23 is directly input to laser diode LD4. Therefore, laser diode LD4 outputs an optical signal which is intensity-modulated by modulation frequency f1. The generated optical signal is branched into two by half mirror 27. One signal is incident on one end of reference fiber 61 through reference optical signal output terminal REF OUT, while the other signal goes to prism 28 through optical switches 261 to 263 to reflect it toward one end of measurement fiber 62 through measurement optical signal output terminal TEST OUT of transmitter 20.

CPU 21 supplies the channel switching instruction to channel switching circuit 24 and optical switches 261 to 263 to select a new output of channel switching circuit 24. Therefore, one of laser diodes LD2 and LD3 excluding LD1, e.g., LD2, is driven upon input of modulation signal f1. The optical signal generated by LD2 is reflected by the corresponding optical switch, e.g., 262, and propagates toward prism 28. The optical signal reflected by prism 28 is incident on one end of measurement fiber 62 through measurement optical signal output terminal TEST OUT.

The reference optical signal and measurement optical signal respectively output from reference optical fiber 61 and measurement optical fiber 62 are received by APDs 43 and 44 while signal levels are controlled by programmable optical attenuators 41 and 42. Timing signal obtaining circuit 496 which comprises the PLL and is connected to the output terminal of filter 50, separates the synchronizing signal added to the reference signal. More specifically, the 270-Hz rectangular wave signal is integrated, and the signal level is detected by a comparator (not shown), thereby obtaining a timing signal shown in FIG. 7C. The timing signal is supplied to synchronizing signal regenerating circuit 495.

At this time, circuit 495 supplies, to CPU 53, a signal indicating that the timing signal is received. Upon reception of this signal, CPU 53 generates a regenerated synchronizing signal so as to turn on switch S21 for a predetermined period of time. When switch S21 is turned on, local signal f1' is supplied from local signal generating circuit 491 to mixers 47 and 48 through switch S21. Thus, the reference optical signal and the measurement optical signal received by receiver 40 are frequency-converted. The converted signals are supplied to phase discrimination circuit 52 to measure a phase difference therebetween.

CPU 21 supplies the switching instruction to channel switching circuit 24 and optical switches 26 until all laser diodes LD1 to LD4 are selected. Thus, the reference optical signal and measurement optical signal are repetitively input to fibers 61 and 62 until all of laser diodes LD1 to LD4 are selected.

In this case, in receiver 40, as the synchronizing signal has already been obtained, even if new channel switching is performed at channel switching circuit 24 of transmitter 20, same local signal f1' is kept supplied to mixers 47 and 48 until all laser diodes LD1 to LD4 are selected.

Figures 7A, 7B, 7C:
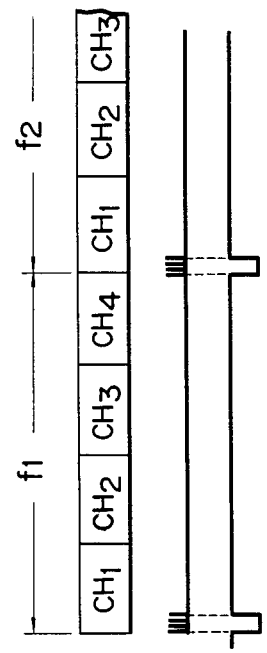
FIGS. 7A to 7C are timing charts showing synchronous relationships in the chromatic dispersion measuring system of the present invention.

As shown in FIG. 7A, after the predetermined period of time has passed, CPU 21 supplies a new selection instruction to modulation signal generating circuits 221 to 224. Thus, the quartz oscillator having a frequency different from modulation frequency f1, e.g., f2=50 MHz, is driven. More specifically, CPU 21 supplies an instruction for generating modulation signal f2 to synchronizing signal generating circuit 211. As described above, circuit 211 ON/OFF-controls switch S12 for one second after signal f2 is generated. Thus, a synchronizing signal is added to modulation signal f2, and resultant modulation signal f2 with the synchronizing signal is supplied to 2-branching circuit 23. Therefore, receiver 40 regenerates the synchronizing signal, and turns on switch S22 for a predetermined period of time, thus supplying local signal f2' to mixer 47 and 48.

Figure 6A:
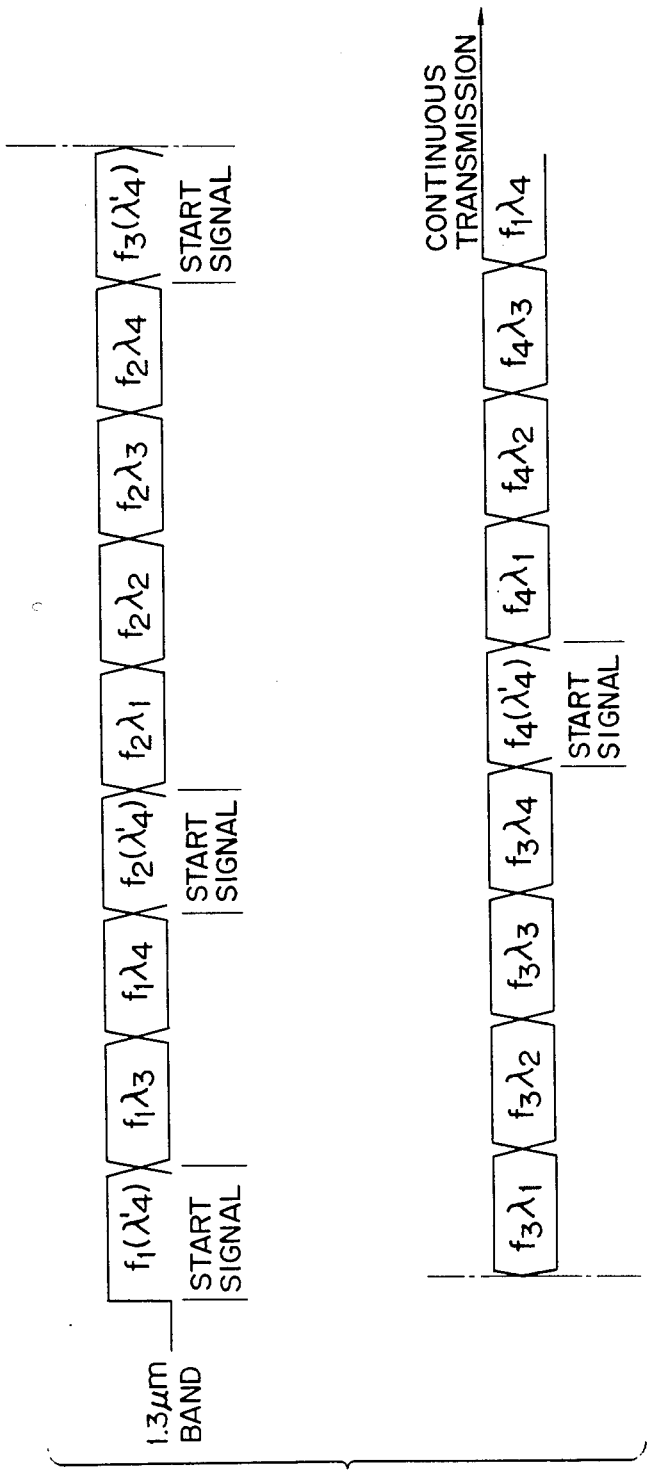
FIGS. 6A and 6B are timing charts showing transmission timings of a modulation signal, and respectively showing a case wherein a 1.3-$\mu$m band zero dispersion wavelength optical fiber is used and a case wherein a 1.55-$\mu$m band zero dispersion wavelength optical fiber is used.
Figure 6B:
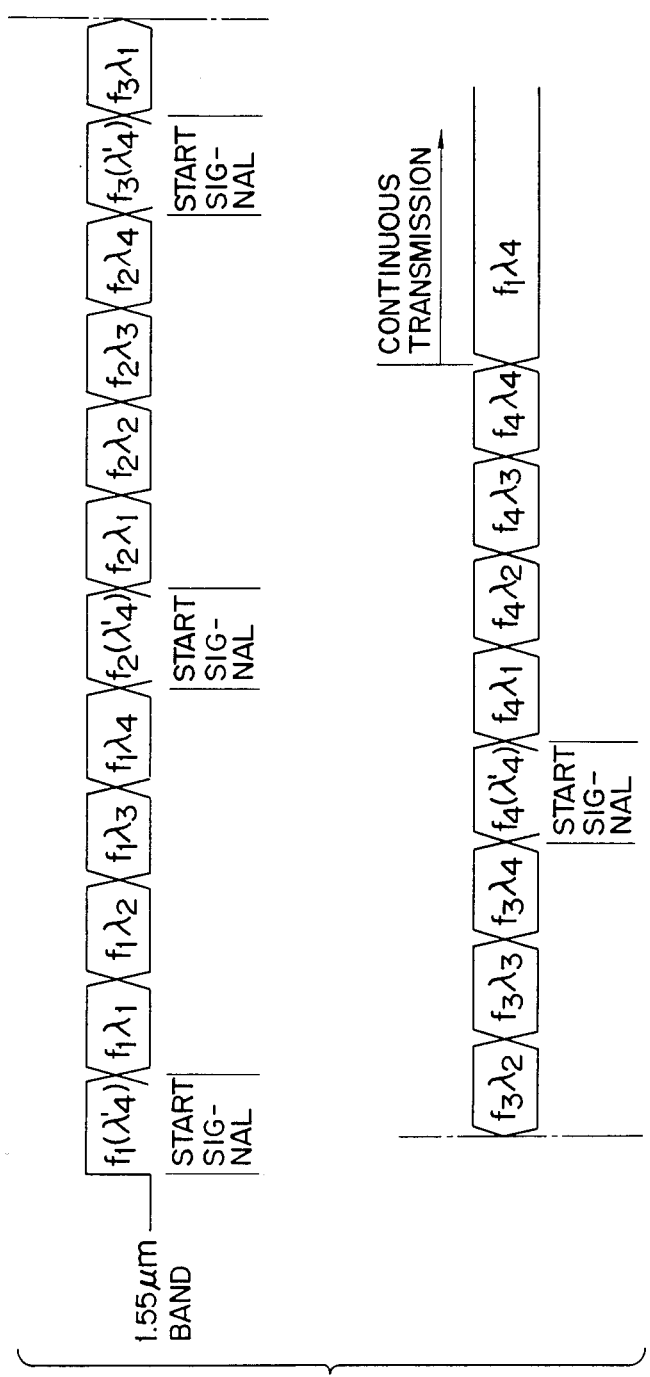

FIGS. 6A and 6B are timing charts showing states wherein modulation signals f1 to f4 are sequentially transmitted. FIG. 6A exemplifies a 1.3-μm band zero dispersion wavelength optical fiber, and FIG. 6B exemplifies a 1.55-μm band zero dispersion wavelength optical fiber.

Figure 2:
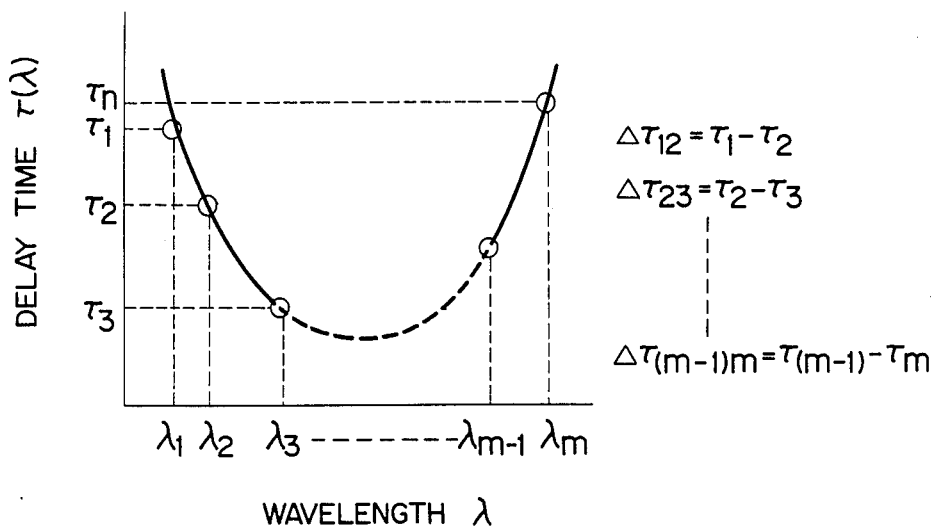
FIG. 2 is a graph showing the relationship between a group delay time difference and wavelengths when the chromatic dispersion are measured based on the principle of the present invention.

The baseband phase comparison method of the chromatic dispersion measuring system of the present invention will be described more in detail with reference to the graph shown in FIG. 2. In the system of the present invention, four wavelengths $\lambda_1$ to $\lambda_4$ are used. However, as shown in FIG. 2, a plurality of light sources having m different wavelengths $\lambda_l$ to $\lambda_m$ are assumed. A phase difference between two adjacent wavelength inside a measuring device (internal phase difference) is given by $\theta'(n-1)n$ ($n=2, 3, \ldots, m$), and a phase difference between two adjacent wavelengths in the receiver after transmission through a measurement optical fiber is given by $\theta_{(n-1)n}$ ($n=2, 3, \ldots, m$). A modulation frequency is given by f, and a delay time difference is given by $\tau_{(n-1)n}$. Therefore, $\theta_{(n-1)n} = \theta'(n-1)n + 2\pi f \tau_{(n-1)n}$ ($n=2, 3, \ldots, m$) is established. Assuming that the length of the measurement optical fiber is given by l, and the phase difference between two wavelengths is given by $\phi_{(n-1)n}$, since $\phi_{(n-1)n} = \theta_{(n-1)n} - \theta'(n-1)n$, group delay time difference $\Delta\tau_{(n-1)n}$ per unit length can be represented by:

$$\Delta\tau_{(n-1)n} = \frac{\phi_{(n-1)n}}{2\pi f} \frac{1}{l}$$

($n=2, 3, \ldots, m$)

The graph in FIG. 2 represents the relationship between group delay time difference $\Delta\tau_{(n-1)n}$ and wavelengths $\lambda_l$ to $\lambda_m$. The curve in FIG. 2 can be represented by some approximating formulas. However, in the chromatic dispersion measuring system of the present invention, since four light sources are used, the following quadratic formula is used:

$$\tau(\lambda) = a\lambda^2 + b + c\lambda^{-2}$$

Phase measurement in the chromatic dispersion characteristic measuring system of the present invention is performed for each combination of four wavelengths $\lambda_1$ to $\lambda_4$ and four modulation frequencies f1 to f4. Of these combinations, data free from phase rotation and having a maximum one of modulation frequencies f1 to f4 is selected, and the group delay time difference between wavelengths is calculated. Based on the measurement result, CPU 53 calculates the quadratic formula $\tau(\lambda) = a\lambda^2 + b + c\lambda^{-2}$ using a least squares method. The resultant quadratic formula is differentiated with wavelength λ, thus obtaining chromatic dispersion characteristics $D(\lambda) = d\tau(\lambda)/d\lambda$.

As described above, when a modulation signal is generated by optical signal transmitter 20, a synchronizing signal is added to the modulation signal within a predetermined period of time from the generation of the modulation signal. Optical signal receiver 40 frequency-converts the synchronizing signal added to the reference optical signal, and selects a local signal of a predetermined frequency using the regenerated synchronizing signal. Therefore, the synchronizing signal from transmitter 20 can be received by receiver 40 without a manual setting operation, and the local signal can be automatically selected. Accordingly, phase measurement can be performed within a short period of time. Further, desired measurement can be precisely performed while reliably performing synchronization without adversely influencing dispersion measurement of measurement optical fiber 62.

One specific embodiment of the present invention has been described. However, various changes and modifications may be made by those who are skilled in the art within the spirit and scope of the invention.

What is claimed is:

1. A light signal transmitter apparatus for measuring a chromatic dispersion of an optical fiber based on a baseband phase comparison method, said apparatus comprising:

light source means for selectively generating one of measurement optical signals having wavelengths corresponding to n wavelength points to be measured and a reference optical signal in a predetermined combination;

modulation signal generating means for generating at least one modulation signal having a predetermined frequency;

synchronizing signal generating means for generating a synchronizing signal having a predetermined frequency;

adding means, connected to said modulation signal generating means and said synchronizing signal generating means, for adding the synchronizing signal generated by said synchronizing signal generating means to the modulation signal generated by said modulation signal generating means;

first control signal generating means for designating the predetermined combination of one of the measurement optical signals and the reference optical signal;

light source switching means, which is coupled between said light source means, said adding means, and first control signal generating means, for selectively supplying the modulation signal added with the synchronizing signal to the light source means corresponding to the combination of one of the measurement optical signals and the reference optical signal designated in accordance with the first control signal;

second control signal generating means for generating a second control signal having a predetermined synchronous relation with the first control signal; and optical switch means, which has reference optical signal input and measurement optical signal inputs which are arranged in correspondence with said light source means, a measurement optical signal output, and a reference optical signal output, for, in response to the second control signal from said second control signal generating means, commonly outputting, to the measurement optical signal output, the measurement optical signal which is output from the designated one of said light source means and is selectively input to the measurement optical signal inputs, and outputting the reference optical signal from the reference optical signal input to the reference optical signal output.

2. An apparatus according to claim 1, wherein said light source means comprises not less than 4 laser diodes, and one of said laser diodes serves to generate both the reference optical signal and the measurement optical signal.

3. An apparatus according to claim 1, wherein said modulation signal generating means comprises not less than 4 quartz oscillators.

4. An apparatus according to claim 1, wherein said adding means comprises not less than 4 switches.

5. An apparatus according to claim 1, wherein said first and second control signal generating means comprise a CPU.

6. An apparatus according to claim 1, wherein said optical switch means comprises a half mirror.

7. A light signal receiver apparatus for measuring a chromatic dispersion of an optical fiber based on a baseband phase comparison method, said apparatus comprising:

first photoelectric conversion means for receiving a reference optical signal which is modulated by a modulation signal added with a synchronizing signal and converting the reference optical signal into a reference electrical signal added with the synchronizing signal;

second photoelectric conversion means for receiving a measurement optical signal which is modulated by a modulation signal added with a synchronizing signal and converting the measurement optical signal into a measurement electrical signal added with the synchronizing signal;

synchronizing signal regenerating means for generating a regenerated synchronizing signal at a predetermined timing;

local signal generating means for generating at least one local signal having a predetermined frequency;

adding means, coupled to said local signal generating means and said synchronizing signal regenerating means, for adding the regenerated synchronizing signal to the local signal from said local signal generating means;

first demodulating means, coupled to said first photoelectric conversion means and said adding means, for receiving the local signal added with the regenerated synchronizing signal and receiving the reference electrical signal added with the synchronizing signal from said first photoelectric conversion means so as to perform local of the reference electrical signal added with the synchronizing signal;

second demodulating means, coupled to said second photoelectric conversion means and said adding means, for receiving the local signal added with the regenerated synchronizing signal and receiving the measurement electrical signal added with the synchronizing signal from said second photoelectric conversion means so as to perform local of the measurement electrical signal added with the synchronizing signal; and timing signal obtaining means, connected to said second demodulating means and said synchronizing signal regenerating means, for separating the synchronizing signal from the reference electrical signal added with the synchronizing signal from said first photoelectric conversion means to obtain a timing signal serving as the synchronizing signal, in order to provide the predetermined timing to said synchronizing signal regenerating means.

8. An apparatus according to claim 7, wherein said timing signal obtaining means comprises a PLL.

9. An apparatus according to claim 7, wherein said local signal generating means comprises not less than 4 quartz oscillators.

10. An apparatus according to claim 7, wherein said adding means comprises not less than 4 switches.

11. A system for measuring a chromatic dispersion of an optical fiber based on a baseband phase comparison method, said system comprising:

a light signal transmitter unit comprising light source means for selectively generating one of measurement optical signals having wavelengths corresponding to n wavelength points to be measured and a reference optical signal in a predetermined combination, modulation signal generating means for generating at least one modulation signal having a predetermined frequency, synchronizing signal generating means for generating a synchronizing signal having a predetermined frequency, first adding means, connected to said modulation signal generating means and said synchronizing signal generating means, for adding the synchronizing signal generated by said synchronizing signal generating means to the modulation signal generated by said modulation signal generating means, first control signal generating means for designating the predetermined combination of one of the measurement optical signals and the reference optical signal, light source switching means, which is coupled between said light source means, said adding means, and first control signal generating means, for selectively supplying the modulation signal added with the synchronizing signal to the light source means corresponding to the combination of one of the measurement optical signals and the reference optical signal designated in accordance with the first control signal, second control signal generating means for generating a second control signal having a predetermined synchronous relation with the first control signal, and optical switch means, which has reference optical signal input and measurement optical signal inputs which are arranged in correspondence with said light source means, a measurement optical signal output, and a reference optical signal output, for, in response to the second control signal from said second control signal generating means, commonly outputting, to the measurement optical signal output, the measurement optical signal which is output from the designated one of said light source means and is selectively input to the measurement optical signal input, and outputting the reference optical signal the reference optical signal input to the reference optical signal output;

a reference optical fiber having one end and the other end, the other end of said reference optical fiber being connected to said reference optical signal output of said optical switch means so as to input the reference optical signal to the one end of said reference optical fiber;

a measurement optical fiber having one end and the other end, the other end of said measurement optical fiber being connected to the measurement optical signal output of said optical switch means so as to input the measurement optical signal to the one end of said measurement optical fiber; and a light signal receiver unit comprising first photoelectric conversion means for receiving a reference optical signal which is modulated by a modulation signal added with a synchronizing signal and converting the reference optical signal into a reference electrical signal added with the synchronizing signal, second photoelectric conversion means for receiving a measurement optical signal which is modulated by a modulation signal added with a synchronizing signal and converting the measurement optical signal into a measurement electrical signal added with the synchronizing signal, synchronizing signal regenerating means for generating a regenerated synchronizing signal at a predetermined timing, local signal generating means for generating at least one local signal having a predetermined frequency, second adding means, coupled to said local signal generating means and said synchronizing signal regenerating means, for adding the regenerated synchronizing signal to the local signal from said local signal generating means, first demodulating means, coupled to said first photoelectric conversion means and said second adding means, for receiving the local signal added with the regenerated synchronizing signal and receiving the reference electrical signal added with the synchronizing signal from said first photoelectric conversion means so as to perform demodulation of the reference electrical signal added with the synchronizing signal, second demodulating means, coupled to said second photoelectric conversion means and said second adding means, for receiving the local signal added with the regenerated synchronizing signal and receiving the measurement electrical signal added with the synchronizing signal from said second photoelectric conversion means so as to perform demodulation of the measurement electrical signal added with the synchronizing signal, and timing signal obtaining means, connected to said second demodulating means and said synchronizing signal regenerating means, for separating the synchronizing signal from the reference electrical signal added with the synchronizing signal from said first photoelectric conversion means to obtain a timing signal serving as the synchronizing signal, in order to provide the predetermined timing to said synchronizing signal regenerating means.

12. A system according to claim 11, wherein said light source means comprises not less than 4 laser diodes, and one of said laser diodes serves to generate both the reference optical signal and the measurement optical signal.

13. A system according to claim 11, wherein said modulation signal generating means comprises not less than 4 quartz oscillators.

14. A system according to claim 11, wherein said first adding means comprises not less than 4 switches.

15. A system according to claim 11, wherein said first and second control signal generating means comprise a CPU.

16. A system according to claim 11, wherein said optical switch means comprises a half mirror.

17. A system according to claim 11, wherein said timing signal obtaining means comprises a PLL.

18. A system according to claim 11, wherein said local signal generating means comprises not less than 4 quartz oscillators.

19. A system according to claim 11, wherein said second adding means comprises not less than 4 switches.

* * * * *